US011472832B2

(12) United States Patent
Shaw et al.

(10) Patent No.: US 11,472,832 B2
(45) Date of Patent: Oct. 18, 2022

(54) WITHANOLIDES USEFUL FOR THE TREATMENT OF NEURODEGENERATIVE DISEASES

(71) Applicants: ARNA Therapeutics Inc., Vancouver (CA); Universite Laval, Quebec (CA)

(72) Inventors: Anthony A. Shaw, Vancouver (CA); Jean-Pierre Julien, Quebec (CA); Agnes H. Chan, Vancouver (CA)

(73) Assignees: ARNA Therapeutics Inc., Vancouver (CA); Universite Laval, Quebec City (CA)

( * ) Notice: Subject to any disclaimer, the term of this patent is extended or adjusted under 35 U.S.C. 154(b) by 0 days.

(21) Appl. No.: 16/449,131

(22) Filed: Jun. 21, 2019

(65) Prior Publication Data

US 2019/0315798 A1 Oct. 17, 2019
US 2020/0325168 A9 Oct. 15, 2020

Related U.S. Application Data

(62) Division of application No. 15/038,927, filed as application No. PCT/US2014/067436 on Nov. 25, 2014, now Pat. No. 10,351,590.

(60) Provisional application No. 61/908,455, filed on Nov. 25, 2013.

(51) Int. Cl.
 *C07J 71/00* (2006.01)
(52) U.S. Cl.
 CPC .................................. *C07J 71/001* (2013.01)
(58) Field of Classification Search
 CPC ..................................................... C07J 71/001
 See application file for complete search history.

(56) References Cited

U.S. PATENT DOCUMENTS

2011/0230551 A1  9/2011  Gunatilaka et al.
2012/0196815 A1  8/2012  Timmermann et al.

FOREIGN PATENT DOCUMENTS

WO  2010/030395 A2  3/2010
WO  2010/053655 A2  5/2010
WO  2012/174666 A1  12/2012

OTHER PUBLICATIONS

Swarup, "Pathological hallmarks of amyotrophic lateral sclerosis/frontotemporal lobar degeneration in transgenic mice produced with TDP-43 genomic fragments" Brain : a journal of neurology (2011), 134(Pt 9), 2610-26.*
Nazem "Rodent models of neuroinflammation for Alzheimer's disease"Journal of Neuroinflammation (2015) 12:74, pp. 1-15.*
Wyss-Coray "Inflammation in Alzheimer disease: driving force, bystander or beneficial response?" Nature Medicine 2006 12 (9), 1005.*
C. Lutz "Mouse models of ALS: Past, present and future" Brain Research 1693 (2018) 1-10.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Chiba "Emerging Therapeutic Strategies in Alzheimer's Disease" Intech 2013, 181-225.*
Julien, J.-P. "Transgenic mouse models of amyotrophic lateral sclerosis" Biochimica et Biophysica Acta 1762 (2006) 1013-1024.*
Dawson "Animal models of neurodegenerative diseases" Nature Neuroscience 2018 vol. 21, 1370-1379.*
Picher-Martel et al. "From animal models to human disease: a genetic approach for personalized medicine in ALS" Acta Neuropathologica Communications (2016) 4:70 pp. 1-29.*
Adam, Octavian R. "Symptomatic Treatment of Huntington Disease" Neurotherapeutics: The Journal of the American Society for Experimental NeuroTherapeutics Apr. 2008, vol. 5, 181-197.*
Georg Pilz, "Modern multiple sclerosis treatment—what is approved, what is on the horizon" Drug Discovery Today Dec. 2008, vol. 13, Nos. 23/24 1013-1025.*
Crosio "Astroglial Inhibition of NF-kB Does Not Ameliorate Disease Onset and Progression in a Mouse Model for Amyotrophic Lateral Sclerosis (ALS)" PLoS ONE Mar. 2011 | vol. 6 | Issue 3 | e17187.*
Ciryam "A transcriptional signature of Alzheimer's disease is associated with a metastable subproteome at risk for aggregation" PNAS |Apr. 26, 2016, vol. 113 No. 17, 4753-4758.*
Musunuri "Quantification of the Brain Proteome in Alzheimer's Disease Using Multiplexed Mass Spectrometry" J. Proteome Res. 2014, 13, 2056-2068.*
Petrov "ALS Clinical Trials Review: 20 Years of Failure. Are We Any Closer to Registering a New Treatment?" Frontiers in Aging Neuroscience | www.frontiersin.org Mar. 1, 2017 | vol. 9 | Article 68, 1-11 p. 4.*
Jiang "Amyloid fibrils in FTLD-TDP are composed of TMEM106B and not TDP-43" 304 | Nature | vol. 605 | May 12, 2022.*
Dorwald, "Side Reactions in Organic Synthesis," *Wiley*: VCH, Weinheim p. IX of Preface pp. 1-16 (2005).
Fuska et al., "Microbial transformations of natural antitumor agents. 23. Conversion of withaferin-A to 12β- and 15β-hydroxy derivatives of withaferin-A," *Steroids, Elsever Science Publishers* 40(2):157-169 (1982).
International Search Report and Written Opinion of the International Searching Authority, dated Feb. 11, 2015, for International Application No. PCT/US2014/067436, 18 pages.
Llanos et al., "Withaferin A-related steroids from *Withania aristata* exhibit potent antiproliferative activity by inducing apoptosis in human tumor cells," *European Journal of Medicinal Chemistry* 54:499-511 (2012).
Wijeratne et al., "Structure-Activity Relationships for Withanolides as Inducers of the Cellular Heat-Shock Response," *Journal of Medical Chemistry* 57:2851-2863 (2014).

(Continued)

*Primary Examiner* — David K O'Dell
(74) *Attorney, Agent, or Firm* — Seed IP Law Group LLP

(57) ABSTRACT

Provided herein are synthetic analogs of withanolide natural products and their pharmaceutical uses in treating neurodegenerative diseases.

9 Claims, 4 Drawing Sheets

(56) References Cited

OTHER PUBLICATIONS

Wisclicenus, "Adolph Strecker's Short Textbook of Organic Chemistry," *Spottiswoode*: London, pp. 38-39 (1881).
Yokota et al., "Development of withaferin A analogs as probes of angiogenesis," *Bioorganic & Medicinal Chemistry Letters* 16:2603-2607 (2006).
Swamp et al., "Deregulation of TDP-43 in amyotrophic lateral sclerosis triggers nuclear factor κB-mediated pathogenic pathways," *J. Exp. Med.* 208(12):2429-2447, 2011.
Wilson et al., "TDP-43 in aging and Alzheimer's disease—a review," *Int. J. Clin. Exp. Pathol.* 4(2): 147-155, 2011.

\* cited by examiner

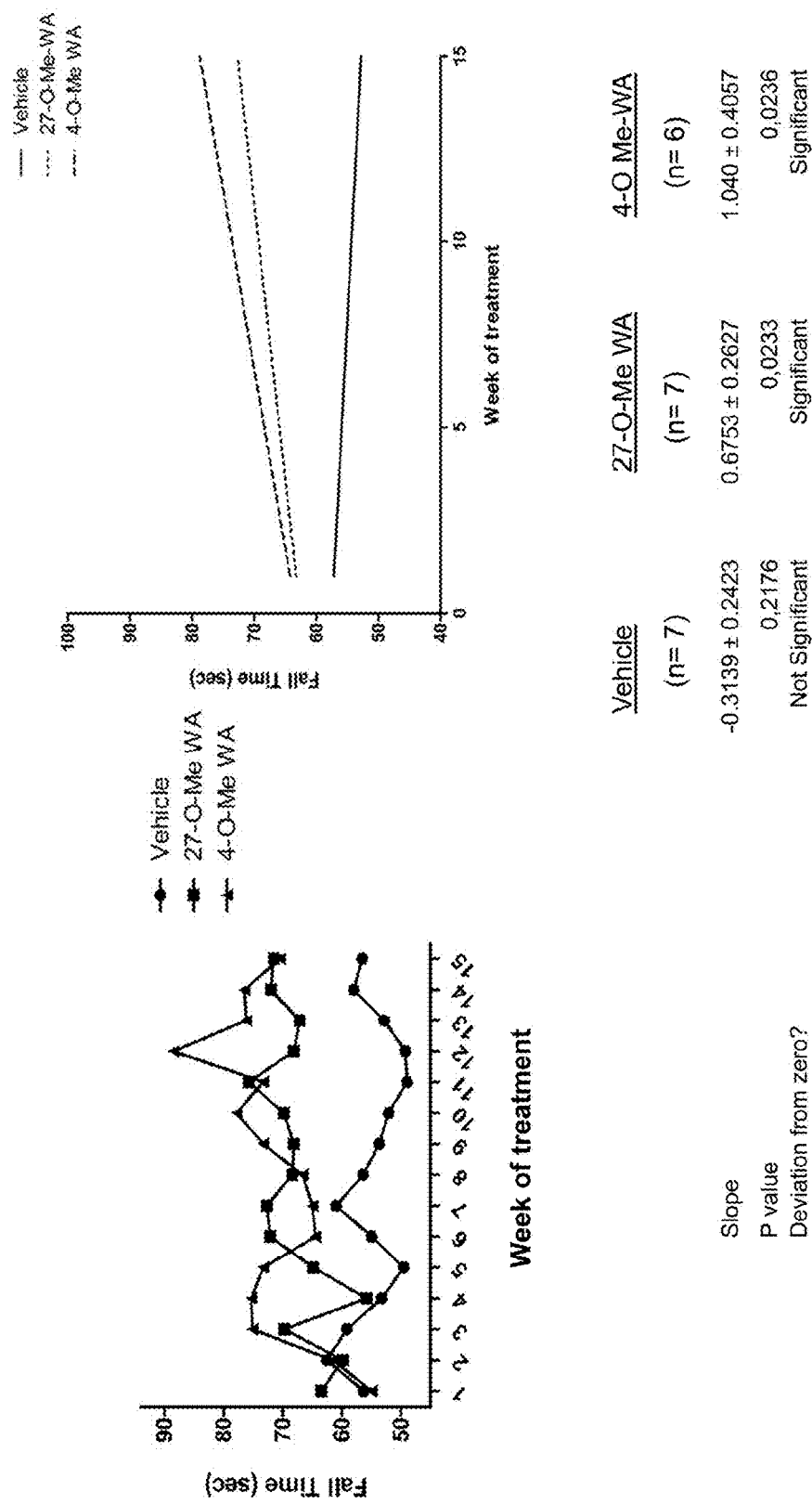

WITHANOLIDES USEFUL FOR THE TREATMENT OF NEURODEGENERATIVE DISEASES

CROSS-REFERENCE TO RELATED APPLICATION

This application is a divisional of U.S. application Ser. No. 15/038,927, filed May 24, 2016 (now allowed), which is a 371 national phase application of International Application No. PCT/US2014/067436 filed Nov. 25, 2014, which claims the benefit under 35 U.S.C. § 119(e) of U.S. Provisional Patent Application No. 61/908,455 filed Nov. 25, 2013, which applications are incorporated herein by reference in their entirety.

BACKGROUND

Technical Field

This application relates to synthetic analogs of withanolide natural products and their pharmaceutical uses.

Description of the Related Art

Neurodegenerative diseases are characterized by selective neurodegeneration in specific regions of the brain and spinal cord. Amyotrophic Lateral Sclerosis (ALS), commonly known as "Lou Gehrig's disease", is a progressive neurodegenerative disease of unknown etiology. The disease progressively impairs an individual's ability to control voluntary muscle movement. The disease tends to progress rapidly, leading to paralysis and death within 2-5 years of diagnosis in most cases. There are currently few therapeutic options for patients suffering from ALS. The only FDA approved drug for the treatment of ALS is Rilutek®, introduced in 1995, which extends life expectancy in individuals with ALS for a few months.

A number of hypotheses have been advanced concerning the pathogenesis of ALS. One is that glutamate, the most abundant excitatory neurotransmitter in the central nervous system (CNS), causes neuronal cell death when its levels are chronically elevated. Glutamate levels have been shown to be elevated in ALS patients (A. Platitakis and J. T. Caroscio, *Ann. Neurol.* 1987, 22: 5575-579). Oxidative stress is another area of focus in ALS research. The potential importance of antioxidant dysfunction was triggered by the discovery that superoxide dismutase (SOD)1 mutations are associated with the familial form of ALS (D. R. Rosen et al., 1993, *Nature*, 362: 59-62) which account for about 20% of cases. An autoimmune mechanism is another potential ALS pathogenesis (M. R. Pagani et al. *Neurol. Res. Int.*, 2011, 2011:497080). Abnormal protein mis-folding and aggregation have recently gained recognition as an underlying pathogenic mechanism in ALS and several other neurodegenerative diseases. Intracellular proteins that exhibit conformational mis-folding in ALS include SOD1 and transactive response (TAR) DNA-binding protein-43 (TDP-43).

Several years ago it was demonstrated that abnormalities in TDP-43, a highly-conserved nuclear protein, were closely associated with ALS (T. Arai et al, 2006, *Biochem. Biophys. Res. Commun.*, 351: 602-611). In healthy nerve cells, TDP-43 intracellular distribution is restricted to the nuclear region. However, in ALS-affected neuronal cells, TDP-43 was also prominently present within cytoplasmic aggregates. Further, it was shown that neuropathology-associated TDP-43 was atypically phosphorylated, extensively ubiquitinated, and proteolytically cleaved to generate carboxyl-terminus fragments in affected brain regions (M. Neumann et al., 2006, *Science* 314:130-133). Thus, the modified TDP-43 accumulation patterns as well as intracellular processing abnormalities were proposed as contributors to degenerative neuronal cell changes in ALS. These and other abnormalities related to TDP-43 are referred to herein as TDP-43 proteinopathies.

A relatively recent discovery related to TDP-43 has provided fundamental insights into pathogenic mechanisms operative in ALS. Studies performed at Laval University showed that TDP-43 was unexpectedly associated with the p65 sub-unit of the nuclear factor-κB (NF-κB) inflammation-regulating transcription factor in spinal cord samples obtained from ALS patients (V. Swamp et al., 2011, 1 Exp. Med., 208:2429-2447).

Activation of the NF-κB signalling pathway is triggered by a number of stimuli including reactive oxygen species, various pro-inflammatory cytokines including interleukin-1 (IL-1) and tumor necrosis factorγα (TNFα) as well as different bacterial products (S. Vallabhapurapu and M. Karin, 2009, *Annu. Rev. Immunol.*, 27: 693-733; L. Verstrepen et al., 2008, *Cell. Mol. Life Sci.* 65: 2964-29678). NF-κB activity is primarily restrained by its physical interaction with inhibitory IκB proteins. In resting cells, NF-κB is present as a latent, inactive, IκB-bound complex in the cytoplasm. When a cell receives a threshold level of one of these signals, NF-κB is rapidly liberated from IκB, enters the nucleus and activates transcription of specific genes, many of which encode pro-inflammatory and immune-response regulatory proteins. Almost all signals that trigger the NF-κB signalling pathway converge on activation of a molecular complex that contains a serine residue-specific IκB kinase (IKK) (M. Adli et al., 2010, *PLoS One*, 5: e9428). In the classical NF-κB pathway, activation of the IKK complex leads to phosphorylation mediated by IKKβ of two specific serines near the N terminus of IκBα, which subsequently targets IκBα for intracellular ubiquitination and degradation by the 26S proteasome complex (Vallabhapurapu 2009 op cit.; M. Adli 2010 op cit.). Activation of the NF-κB signalling pathway is generally a transient cellular event and tightly regulated (Vallabhapurapu 2009 op cit).

TDP-43 and the p65 chain of NF-κB were shown to have co-immunoprecipitated in cell culture systems, spinal cord extracts from transgenic TDP-43 mice and spinal cord samples prepared from post-mortem ALS patients, but not from matched control samples (Swamp 2011 op. cit.). In mouse and human spinal cord samples, p65 tended to co-localize with TDP-43 in the nuclei of microglia, astrocytes and neurons. TDP-43 mRNA levels were up-regulated by 2.5-fold while NF-κB mRNA was up-regulated by approximately four-fold in ALS spinal cord samples as compared to control subject material (Swamp 2011 op. cit.). Gel-shift assays confirmed that the p65 chain of NF-κB p65 was more likely to bind to its consensus sequence of reporter DNA in the presence of TDP-43. Further, TDP-43 over-expression boosted production of pro-inflammatory cytokines, which heightened neuronal susceptibility to neurotoxic elements. Deletion mutation protein-mapping studies revealed that TDP-43 interacted with the p65 chain component of NF-κB through its N-terminal domain and RNA recognition motif (RMM-1) (Swamp 2011 op. cit.). NF-κB inhibition attenuated the vulnerability of cultured neurons over-expressing TDP-43 to glutamate-induced or microglia cell-mediated toxicity.

Pharmacological intervention with withaferin A (WA) attenuated disease symptoms and ameliorated motor dysfunction in TDP-43 transgenic mice. WA was shown to inhibit TNFα induced activation of IκB kinase β (IKKβ) via a thioalkylation-sensitive redox mechanism (W. Vanden Berghe et al., 2012, *Biochem. Pharmacol.*, 84: 1282-12891). IKKβ Ser-181 hyperphosphorylation induced by WA led to inhibition of IκBα phosphorylation and degradation which prevented NF-κB translocation, NF-κB/DNA binding and gene transcription (M. Kaileh et al., 2007, *J. Biol. Chem.*, 282: 4253-4264).

Withaferin A (WA) was the first withanolide-type compound isolated from leaves of the Withania somifera plant.

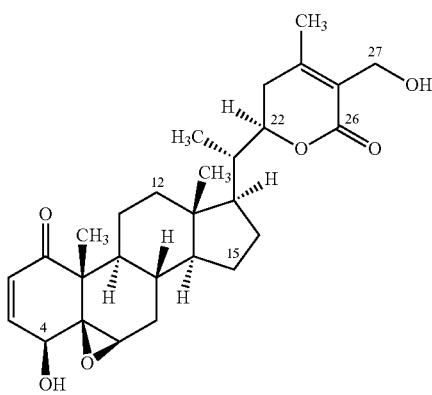

Withaferin A (WA)

This compound has been noted for its anti-inflammatory, anti-tumor, anti-angiogenic and immuno-suppressive activities. WA is a member of withanolides, which are generally described as a group of naturally occurring C28-steroidal lactone triterpenoids built on an intact or rearranged ergostane framework, in which C-22 and C-26 are appropriately oxidized to form a six-membered lactone ring (M. H. Mirjalili et al., *Molecules* 2009, 14(7): 2373-2393). Numerous analogs of WA have been purified from withanolide-containing plant material, synthesized, or semi-synthetically prepared from the WA starting material (U.S. Pub. No. 2011/0230551).

WA has been proposed as a treatment for neurodegenerative diseases, such as ALS, frontotemporal lobar degeneration, Parkinson's disease and Alzheimer's disease (WO2012/174666) and it has been shown that WA is effective in ameliorating disease progression in mouse models of ALS. An in vivo therapeutic effect of WA through NF-κB inhibition has been demonstrated in four recognized transgenic mouse models of ALS.

Although WA is a promising therapeutic agent for the treatment of ALS and other neurodegenerative diseases, it has a short half life when administered in vivo, as well as some toxicity. Hence there is a need for novel compounds with improved pharmacokinetic, bio-distribution and safety profiles.

BRIEF DESCRIPTION OF THE SEVERAL VIEWS OF THE DRAWINGS

FIG. 4A shows the accelerating rotarod performance of TDP-43 A315T mice treated with vehicle, 4-O-Methyl WA or 27-O-Methyl WA analogs over a 15 week period.

FIG. 4B shows the linear regression analysis of the data in FIG. 4A.

SUMMARY

Figure 1A:
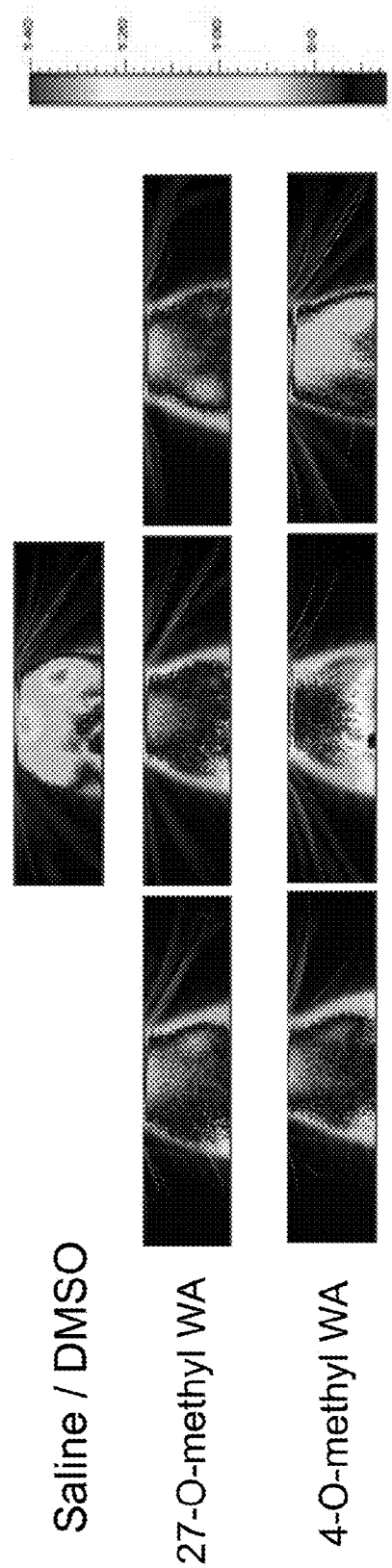
FIG. 1A shows bioluminescense imaging of the brains of GFAP-luciferase transgenic mice after exposure to lipopolysaccharide (LPS) followed by treatment with saline or the withanolide compounds 4-O-methyl WA or 27-O-methyl WA.

Described herein are semi-synthetic analogs of withaferin A and methods for using the analogs for the prophylaxsis or treatment of neurodegenerative diseases or conditions such as Amyotrophic Lateral Sclerosis (ALS), frontotemporal lobar degeneration (FTLD), Parkinson's disease, Alzheimer's disease and mild cognitive impairment.

Accordingly, in one aspect, the invention is directed to compounds of Formula (I):

Formula (I)

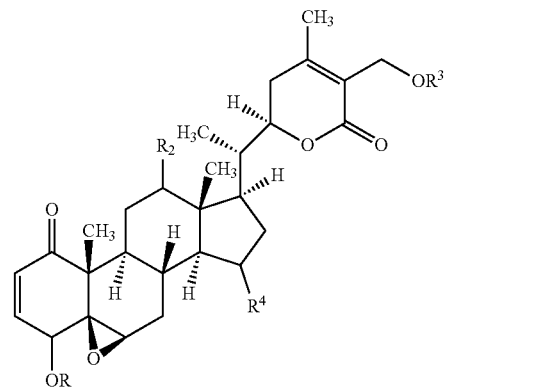

wherein:
$R^1$ is hydrogen, alkyl, alkenyl, haloalkyl, aralkyl, heterocyclylalkyl, —$R^a$—$OR^b$, —$C(O)R^b$, cycloalkylalkyl or —$P(O)_2O^{2-}$;

$R^2$ is hydrogen, alkyl, alkenyl, haloalkyl, —$OR^b$ or —$OC(O)R^b$;

$R^3$ is hydrogen, alkyl, alkenyl, haloalkyl, aralkyl, heterocyclylalkyl, —$R^a$—$OR^b$, —$C(O)R^b$, cycloalkylalkyl or —$P(O)_2O^{2-}$;

$R^4$ is hydrogen, alkyl, alkenyl, haloalkyl, —$OR^b$ or —$OC(O)R^b$;

$R^a$ is an alkylene or alkenylene chain; and $R^b$ is hydrogen, alkyl, alkenyl, haloalkyl, aralkyl, cycloalkylalkyl or heterocyclylalkyl, as an isolated stereoisomer or mixture thereof, or a pharmaceutically acceptable salt thereof, provided that, when $R^2$ and $R^4$ are each hydrogen, $R^1$ and $R^3$ cannot both be selected from the group consisting of hydrogen and —$C(O)CH_3$; or when $R^1$ and $R^3$ are each —C(O)CH$_3$, $R^2$ or $R^4$ cannot both be selected from the group consisting of hydrogen and —OC(O)CH$_3$.

In some embodiments, the compounds are of formula (I) wherein $R^2$ and $R^4$ are each hydrogens, and the compounds have a structure represented by Formula (Ia):

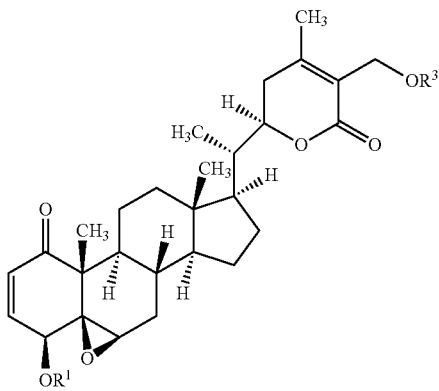

Formula (Ia)

wherein:
$R^1$ is hydrogen, alkyl or alkenyl; and
$R^3$ is hydrogen, alkyl or alkenyl.

In further embodiments, the compounds are: 27-O-methylwithaferin A ($R^1$ is hydrogen and $R^3$ is methyl), 4-O-methylwithaferin A ($R^1$ is methyl and $R^3$ is hydrogen), and 4,27-O-dimethylwithaferin A ($R^1$ is methyl and $R^3$ is methyl).

Another aspect of the invention is directed to a pharmaceutical composition comprising a compound of formula (I) or formula (Ia) and a pharmaceutically acceptable excipient.

In another aspect, the invention is directed to a method of treating or preventing a disease characterized by TDP-43 proteinopathy in a patient comprising administering to a patient in need thereof a therapeutically or prophylactically effective amount of a compound of formula (I) or formula (Ia).

In another aspect, the invention is directed to a method of treating or preventing amyotrophic lateral sclerosis in a patient comprising administering to a patient in need thereof a therapeutically or prophylactically effective amount of a compound of formula (I) or formula (Ia).

In a further aspect, the invention is directed to a method of treating or preventing Alzheimer's disease in a patient comprising administering to a patient in need thereof a therapeutically or prophylactically effective amount of a compound of formula (I) or formula (Ia).

In a further aspect, the invention is directed to a method of treating or preventing Parkinson's disease in a patient comprising administering to a patient in need thereof a therapeutically or prophylactically effective amount of a compound of a formula (I) or formula (Ia).

In another aspect, the invention is directed to method of treating or preventing motor neuron disease in a patient comprising administering to a patient in need thereof a therapeutically or prophylactically effective amount of a compound of formula (I) or formula (Ia).

In another aspect, the invention is directed to a method of treating or preventing frontotemporal lobar degeneration in a patient comprising administering to a patient in need thereof a therapeutically or prophylactically effective amount of a compound of formula (I) or formula (Ia).

In another aspect, the invention is directed to a method of treating or preventing mild cognitive impairment or preventing the development of Alzheimer's disease in a patient exhibiting mild cognitive impairment comprising administering to a patient in need thereof a therapeutically or prophylactically effective amount of a compound of Formula (I) or Formula (Ia).

DETAILED DESCRIPTION

Disclosed herein are semi-synthetic analogs of Withaferin A and their various pharmaceutical uses, particularly in treating neurodegenerative diseases, including amyotrophic Lateral Sclerosis (ALS), frontotemporal lobar degeneration (FTLD), Parkinson's disease, mild cognitive impairment (MCI), Alzheimer's disease, and diseases associated with TPD-43 proteinopathy. One embodiment provides a compound of Formula (I):

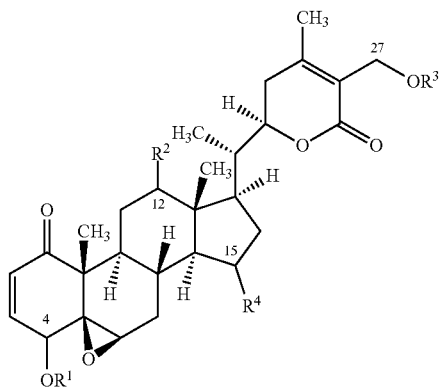

Formula (I)

wherein:
$R^1$ is hydrogen, alkyl, alkenyl, haloalkyl, aralkyl, heterocyclylalkyl, —$R^a$—OR$^b$, —C(O)R$^b$, cycloalkylalkyl or —P(O)$_2$O$^{2-}$;
$R^2$ is hydrogen, alkyl, alkenyl, haloalkyl, —OR$^b$ or —OC(O)R$^b$;
$R^3$ is hydrogen, alkyl, alkenyl, haloalkyl, aralkyl, heterocyclylalkyl, —$R^a$—OR$^b$, —C(O)R$^b$, cycloalkylalkyl or —P(O)$_2$O$^{2-}$;
$R^4$ is hydrogen, alkyl, alkenyl, haloalkyl, —OR$^b$ or —OC(O)R$^b$;
$R^a$ is an alkylene or alkenylene chain; and
$R^b$ is hydrogen, alkyl, alkenyl, haloalkyl, aralkyl, cycloalkylalkyl or heterocyclylalkyl,
as an isolated stereoisomer or mixture thereof, or a pharmaceutically acceptable salt thereof, provided that,
when $R^2$ and $R^4$ are each hydrogen, $R^1$ and $R^3$ cannot both be selected from the group consisting of hydrogen and —C(O)CH$_3$; or
when $R^1$ and $R^3$ are each —C(O)CH$_3$, $R^2$ or $R^4$ cannot both be selected from the group consisting of hydrogen and —OC(O)CH$_3$.

In various embodiments, the compound of Formula (I) comprises one or more alkyl ether moieties, in particular, at the C-4, C-27 or both locations. In certain embodiments, W and $R^3$ are independently lower alkyl or alkenyl. In further embodiments, $R^1$ and $R^3$ are independently methyl.

In various embodiments, $R^2$ and $R^4$ are each hydrogens, and the compound of Formula (I) has a structure represented by Formula (Ia):

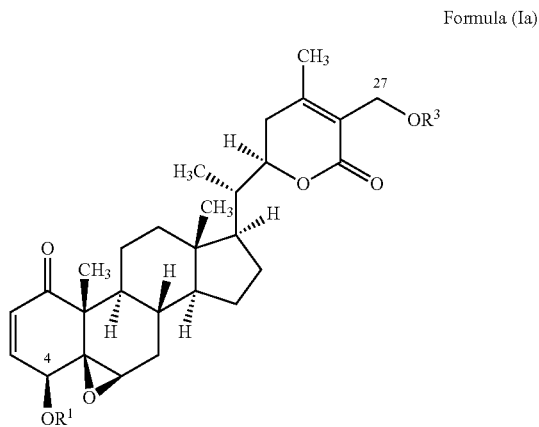

Formula (Ia)

wherein:
$R^1$ is hydrogen, alkyl or alkenyl; and
$R^3$ is hydrogen, alkyl or alkenyl.

In further embodiments, the compounds are: 27-O-methylwithaferin A ($R^1$ is hydrogen and $R^3$ is methyl), 4-O-methylwithaferin A ($R^1$ is methyl and $R^3$ is hydrogen), and 4,27-O-dimethylwithaferin A ($R^1$ is methyl and $R^3$ is methyl)

Each individual compound disclosed in U.S. Pub. No. 2011/0230551 is expressly excluded from the scope of Formulae (I) and (IIa).

Another embodiment provides a pharmaceutical composition comprising a compound of Formula (I) or Formula (Ia), as defined herein, and a pharmaceutically acceptable excipient.

Various embodiments further provide pharmaceutical use of the compound of Formula (I) or (Ia). More specifically, the pharmaceutical uses of the compound or composition comprising the same include the treatment of neurodegenerative diseases, or prevention of the progression or worsening of neurodegenerative diseases. In particular, the neurodegenerative disease is characterized by TDP-43 proteinopathy.

Thus, one embodiment provides a method of treating or preventing a disease characterized by TDP-43 proteinopathy in a patient comprising administering to a patient in need thereof a therapeutically or prophylactically effective amount of a compound of Formula (I) or Formula (Ia).

A further embodiment provides a method of treating or preventing amyotrophic lateral sclerosis in a patient comprising administering to a patient in need thereof a therapeutically or prophylactically effective amount of a compound of Formula (I) or Formula (Ia).

Another embodiment provides a method of treating or preventing Alzheimer's disease in a patient comprising administering to a patient in need thereof a therapeutically or prophylactically effective amount of a compound of Formula (I) or Formula (Ia).

Another embodiment provides a method of treating or preventing Parkinson's disease in a patient comprising administering to a patient in need thereof a therapeutically or prophylactically effective amount of a compound of Formula (I) or Formula (Ia).

Another embodiment provides a method of treating or preventing motor neuron disease in a patient comprising administering to a patient in need thereof a therapeutically or prophylactically effective amount of a compound of Formula (I) or Formula (Ia).

Another embodiment provides a method of treating or preventing frontotemporal lobar degeneration in a patient comprising administering to a patient in need thereof a therapeutically or prophylactically effective amount of a compound of Formula (I) or Formula (Ia).

Another embodiment provides a method of treating or preventing mild cognitive impairment or preventing the development of Alzheimer's disease in a patient exhibiting mild cognitive impairment comprising administering to a patient in need thereof a therapeutically or prophylactically effective amount of a compound of Formula (I) or Formula (Ia).

Definitions

As used in the specification and appended claims, unless specified to the contrary, the following terms have the meaning indicated:

"Amino" refers to the —$NH_2$ radical.
"Carboxy" refers to the —C(O)OH radical.
"Cyano" refers to the —CN radical.
"Nitro" refers to the —$NO_2$ radical.
"Oxo" refers to the =O radical.
"Thioxo" refers to the =S radical.
"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. For purposes of this invention, the term "lower alkyl" refers to an alkyl radical having one to four carbon atoms.

"Alkenyl" refers to a straight or branched hydrocarbon chain radical consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, penta-1,4-dienyl, and the like.

"Alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain.

"Alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain.

"Aryl" refers to a hydrocarbon ring system radical comprising hydrogen, 6 to 14 carbon atoms and at least one aromatic ring. For purposes of this invention, the aryl radical may be a monocyclic, bicyclic, or tricyclic system and which may include spiro ring systems. An aryl radical is commonly, but not necessarily, attached to the parent molecule via an aromatic ring of the aryl radical. Aryl radicals include, but are not limited to, aryl radicals derived from acenaphthylene, anthracene, azulene, benzene, 6,7,8,9-tetrahydro-5H-benzo[7]annulene, fluorene, as-indacene, s-indacene, indane, indene, naphthalene, phenalene, and phenanthrene.

"Aralkyl" refers to a radical of the formula —$R_a$—$R_c$ where $R_a$ is an alkylene chain as defined above and $R_c$ is one or more aryl radicals as defined above. Examples of aralkyl include, without limitation, benzyl, diphenylmethyl and the like.

"Cycloalkyl" refers to a stable non-aromatic monocyclic or polycyclic hydrocarbon radical consisting solely of carbon and hydrogen atoms, which includes fused, spiro or bridged ring systems, having from three to fifteen carbon atoms, preferably having from three to ten carbon atoms, more preferably from five to seven carbons and which is saturated or unsaturated and attached to the rest of the molecule by a single bond. For purposes of this invention, a bridged ring system is a system wherein two non-adjacent ring atoms thereof are connected through an atom or a group of atoms, wherein the atom or the group of atoms are the bridging element. Examples of cycloalkyl include, without limitation, cyclopropyl, cyclobutyl, cyclopentyl, cyclohexyl, cycloheptyl, and cyclooctyl. Polycyclic radicals include fused, spiro or bridged cycloalkyl radicals, for example, $C_{10}$ radicals such as adamantanyl (bridged) and decalinyl (fused), and $C_7$ radicals such as bicyclo[3.2.0]heptanyl (fused), norbornanyl and norbornenyl (bridged), as well as substituted polycyclic radicals, for example, substituted $C_7$ radicals such as 7,7-dimethylbicyclo[2.2.1]heptanyl (bridged), and the like.

"Cycloalkylalkyl" refers to a radical of the formula —$R_aR_d$ where $R_a$ is an alkylene chain as defined above and $R_d$ is a cycloalkyl radical as defined above.

"Halo" refers to fluoro, chloro, bromo or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Heterocyclyl" refers to a stable 3- to 18-membered non-aromatic ring system radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of a bridged heterocyclyl include, but are not limited to, azabicyclo[2.2.1]heptanyl, diazabicyclo[2.2.1]heptanyl, diazabicyclo[2.2.2]octanyl, diazabicyclo[3.2.1]octanyl, diazabicyclo[3.3.1]nonanyl, diazabicyclo[3.2.2]nonanyl and oxazabicyclo[2.2.1]heptanyl. A "bridged N-heterocyclyl" is a bridged heterocyclyl containing at least one nitrogen, but which optionally contains up to four additional heteroatoms selected from O, N and S. For purposes of this invention, a non-bridged ring system is a system wherein no two non-adjacent ring atoms thereof are connected through an atom or a group of atoms. Examples of heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-c]pyridinyl, octahydro-1H-pyrrolo[2,3-b]pyridinyl, octahydro-1H-pyrrolo[3,4-b]pyridinyl, octahydropyrrolo[3,4-c]pyrrolyl, octahydro-1H-pyrido[1,2-a]pyrazinyl, 2-oxopiperazinyl, 2-oxopiperidinyl, 2-oxopyrrolidinyl, oxazolidinyl, 3,7-diazabicyclo[3.3.1]nonan-3-yl, piperidinyl, piperazinyl, 4-piperidonyl, pyrrolidinyl, pyrazolidinyl, quinuclidinyl, thiazolidinyl, tetrahydrofuranyl, thienyl[1,3]dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a]azepinyl, azepanyl, azabicyclo[3.2.1]octyl, and 2,7-diazaspiro[4.4]nonanyl.

"Heterocyclylalkyl" refers to a radical of the formula —$R_a$—$R_e$ where $R_a$ is an alkylene chain as defined above and $R_e$ is a heterocyclyl radical as defined above, and when the heterocyclyl is a nitrogen-containing heterocyclyl, the heterocyclyl may be attached to the alkylene chain at the nitrogen atom.

As used herein, unless specified otherwise, each one of alkyl, alkenyl, haloalkyl, aralkyl, heterocyclylalkyl, alkylene chain, alkenylene chain, cycloalkylalkyl moieties may be optionally substituted, whereby one or more hydrogens are replaced by one or more of the following substituents: amino, halo, cyano, nitro, oxo, thioxo, trialkylsilanyl (including trimethylsilanyl), —$OR^f$, —OC(O)—$R^f$, —$N(R^f)_2$, —C(O)$R^f$, —C(O)O$R^f$, —C(O)N($R^f)_2$, —N($R^f$)C(O)O$R^f$, —N($R^f$)C(O)$R^f$, —N($R^f$)S(O)$_2$R, —S(O)$_t$O$R^f$ (where t is 1 or 2), —S(O)$_p R^f$ (where p is 0, 1 or 2), and —S(O)$_2$N($R^f)_2$ where each $R^f$ is independently selected from the group consisting of alkyl, alkenyl, haloalkyl, aralkyl, heterocyclylalkyl, cycloalkylalkyl.

"Patient" means a mammal who has been diagnosed with a neurodegenerative disease or who is genetically predisposed to such diseases.

"Mammal" means any vertebrate of the class Mammalia. Humans and domestic animals, such as cats, dogs, swine, cattle, sheep, goats, horses, rabbits, and the like are a particular focus. Preferably, for purposes of this invention, the mammal is a primate (e.g., monkey, baboon, chimpanzee and human), and more preferably, the mammal is a human.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of formula (I) or a formulation of a therapeutic agent described herein and a medium generally accepted in the art for the delivery of the biologically active compound to mammals, for example, humans. Such a medium includes all pharmaceutically acceptable carriers, diluents or excipients therefor.

"Neurodegenerative disease" refers to a progressive loss of structure or function of neurons, including death of neurons. Examples of the neurodegenerative diseases include, without limitation, Parkinson's, Alzheimer's, ALS, motor neuron disease and frontotemporal lobar degeneration (FTLD). In particular, the neurodegenerative disease may be characterized by TDP-43 proteinopathy. Neurodegenerative disease also includes mild cognitive impairment (MCI) (described in S. Gautier et al., 2006, *The Lancet* 351: 1262-1270).

"Therapeutically effective amount" refers to that amount of the therapeutic agent sufficient to delay, forestall or minimize the progress of neurodegeneration, or to provide a therapeutic benefit in the treatment or management of neurodegenerative diseases, including the amelioration of symptoms associated with neurodegenerative diseases.

"Prophylactically effective amount" refers to that amount of the prophylactic agent sufficient to result in preventing or forestalling neurodegenerative diseases, particularly in patients who may be genetically predisposed to such diseases. A prophylactically effective amount may refer to the amount of prophylactic agent sufficient to prevent the age-related or early on-set of neurodegenerative diseases.

As used herein, the terms "prevent", preventing" and "prevention" refer to the prevention of the spread or onset of neurodegenerative diseases in a patient.

As used herein, the terms "treat", "treating" and "treatment" refer to delay, forestall or minimize the neurodegenerative process, preferably prior to neurodegenerative diseases such as ALS, Parkinson's, Alzheimer's, FTLD or mild cognitive impairment (MCI) could develop from the neurodegeneration. The terms also refer to management of neurodegenerative diseases, including the amelioration of symptoms associated with neurodegenerative diseases.

The compounds of formula (I) and (Ia), or their pharmaceutically acceptable salts, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Preparation of the Compound of Formula (I)

The following reaction scheme shows a semi-synthetic approach to preparing the compound of Formula (Ia) by using Withaferin A as a starting material. More specifically, Withaferin A (available from Sigma-Aldrich Canada) can be treated with one or more alkylating agents to alkylate the —OH groups of Withaferin A.

REACTION SCHEME

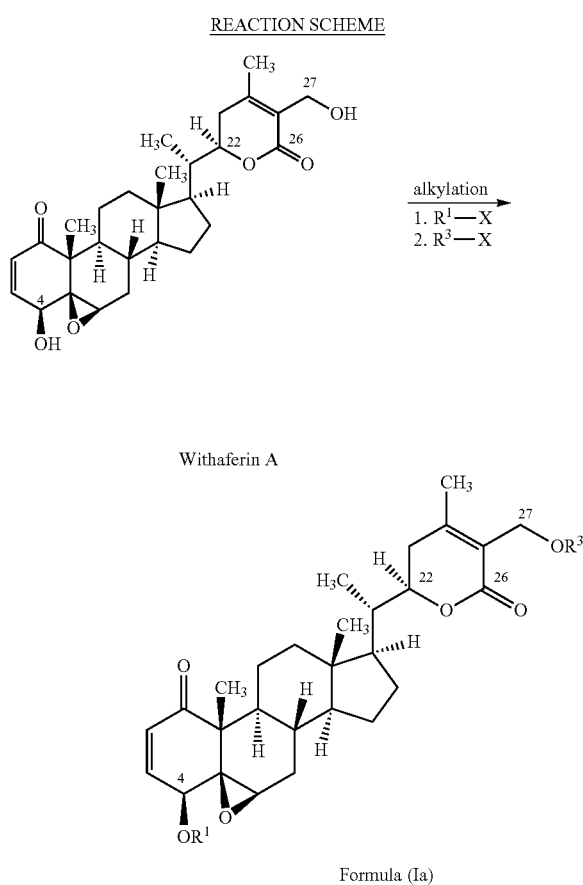

Withaferin A

Formula (Ia)

The reaction may produce a mixture of mono-alkylated compounds at C-4 or C-27 locations, as well as di-alkylated WA at both C-4 and C-27 locations. The alkylated compounds may be separated and isolated by known methods in the art. Where $R^1$ and $R^3$ are identical, a single alkylation step can be carried out. Where $R^1$ and $R^3$ are different, two alkylation steps may be carried out. For example, a stepwise reaction using alkylating agents $R^1$—X and $R^3$—X (X being a leaving group) may be carried out to separately alkylate the hydroxy groups of Withaferin A.

Selective protection of the hydroxy groups at C-4 or C-27 of Withaferin A can direct the alkylation step to a particular location. For instance, the C-4 hydroxy group may be first protected such that the alkylation step only takes place at the C-27 hydroxy group.

Functionalization at the C-12 and C-15 locations of a compound of Formula (I) may be carried out according to the methods disclosed in U.S. Pub. No. 2011/0230551, which reference is incorporated herein by reference in its entirety.

It will be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include benzyl, t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acids include alkyl, aryl or arylalkyl esters.

Protecting groups may be added or removed in accordance with standard techniques, which are known to one of ordinary skill in the art and as described herein. The use of protecting groups is described in detail in Greene, T. W. and P. G. M. Wuts, *Greene's Protective Groups in Organic Synthesis* (1999), 3rd Ed., Wiley. As one of skill in the art would appreciate, the protecting group may also be a polymer resin such as, but not limited to, a Wang resin, Rink resin or a 2-chlorotrityl-chloride resin.

Dosage

The amount of the withanolide compounds required for use in treatment will vary not only with the particular compound selected but also with the route of administration, the nature of the condition for which treatment is required and the age and condition of the patient and will be ultimately determined by a physician. In general, the amount of a compound required for use in treatment will vary not only with the particular compound selected but also with the route of administration, the nature of the condition for which treatment is required and the age and condition of the patient and will be ultimately be determined by a physician. Generally, a suitable dose will be for example in the range of 0.01 to 1000 mg/kg of body weight per day, or for example, in the range of 0.1 to 100 mg/kg/day, or, for example, in the range of 0.5 to 50 mg/kg/day, or for example, in the range of 1 to 25 mg/kg/day. Doses may be administered at appropriate intervals, for example as one, two, three, four or more doses per day. In some cases doses may be administered every day, every two to three days, every four to five days, or every five to seven days. Dosing may continue for days, weeks, months or years, as required.

EXAMPLES

Example 1

Preparation of WA Methyl Ether Analogs from WA

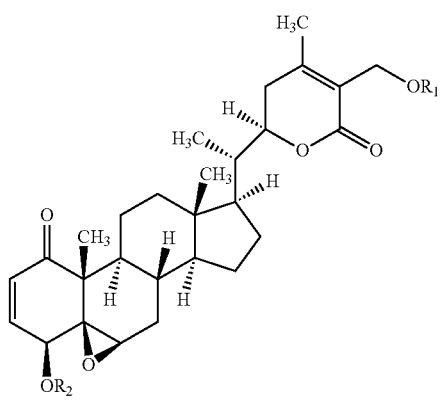

1. Withaferin A: $R_1$=$R_2$=H
2. 27-O-methylwithaferin A: $R_1$=$CH_3$, $R_2$=H
3. 4-O-methylwithaferin A: $R_1$=H, $R_2$=$CH_3$
4. 4,27-O-dimethylwithaferin A: $R_1$=$R_2$=$CH_3$ Preparation 150 mg of Withaferin A (available from Sigma-Aldrich Canada) (WA 1) were treated with sodium hydride in methyl iodide. The reaction produced a mixture of both mono-methylated compounds and di-methylated WA. The reaction mixture was filtered to remove excess sodium hydride and sodium iodide. The filtrate was dried and the residue re-dissolved in dichloromethane. The resulting solution was chromatographed on a silica gel column. Fractions containing the mono-methyl ethers (2 and 3) and dimethyl ether (4) were combined and the compounds separated by reversed phase chromatography.

Pure fractions of each compound were pooled, concentrated, extracted into dichloromethane and dried. Approximately 5-10 mg of each compound was thus obtained, each as a white solid. Spectroscopic data of these compounds are provided in Table 1 below.

TABLE 1

| Compound | m/z [M + H]$^+$ | ∂ ppm (CDCl$_3$) | | | | | |
|---|---|---|---|---|---|---|---|
| | | H-4 | H-27a | H-27b | OH-4 | 4-OMe | 27-OMe |
| Withaferin A (1) | 471 | 3.78 (dd) | 4.41 (dd) | 4.35 (dd) | 2.52 (d) | 2.86 (t) | — | — |
| 27-O-methyl withaferin A (2) | 485 | 3.77 (dd) | 4.29 (d) | 4.17 (d) | 2.50 (d) | — | 3.39 (s) |
| 4-O-methyl withaferin A (3) | 485 | 3.27 (d) | 4.41 (dd) | 4.35 (dd) | — | 2.86 (t) | 3.45 (s) | — |
| 4,27-O-dimethyl withaferin A (4) | 499 | 3.27 (d) | 4.29 (d) | 4.17 (d) | — | — | 3.46 (s) | 3.39 (s) |

Example 2

Brain Bioluminescence in GFAP-Luciferase Mice Exposed to LPS

Two of the novel withanolides were tested for their therapeutic activity in vivo using a transgenic mouse model. Transgenic GFAP-luciferase mice generated in the laboratory of Dr. J. P. Julien were used to assess the ability of the withanolides to inhibit astrogliosis associated with inflammation induced by lipopolysaccharide (LPS) exposure. In vivo bioluminescence imaging was performed to asses the inflammatory response in the cranial region. A decrease in bioluminscense signals in the evaluated region in comparison to the control (saline) indicated that the withanolides had crossed the blood brain barrier and subsequently inhibited gliosis.

Withanolides [4-O-methyl withaferin A (4-O-methyl WA) and 27-O-methyl withaferin A (27-O-methyl WA)] were diluted in 100% dimethyl sulfoxide (DMSO) at a final concentration of 2 mg/ml. GFAP-luc transgenic mice were used to test in vivo the efficacy of these analogs. In these transgenic mice, the firefly luciferase reporter gene is under the control of a 12 kb DNA fragment of the glial fibrillary acidic protein (GFAP) promoter (Caliper Life Sciences). The luciferase reporter is inducible following LPS administration resulting in GFAP transcriptional regulation. If the administration of test compounds following the injection of LPS decreases LPS-induced astrogliosis in GFAP-luc mice, this is visualized as a reduced bioluminescent signal upon imaging.

Transgenic mice under anesthesia were induced to inhale either 5 ul of a solution of LPS (1 mg/ml in 0.9% saline) or a solution of 0.9% saline alone followed 2 h later by an intraperitoneal (i.p.) injection of 0.5 ml of the test compounds (10% dilution in 0.9% saline) at a final concentration of 4 mg/kg. The following day, 2 h before imaging (24 h after the administration of the LPS solution), the transgenic mice were again injected with the withanolides as previously. Twenty minutes prior to imaging, the mice received an i.p. injection of the luciferase substrate D-luciferin (150 mg/kg). D-luciferin was dissolved in 0.9% saline to a final concentration of 20 mg/ml. Mice were anesthetized and imaged using an IVIS 200 imaging system (CaliperLS-Xenogen).

Figure 1B:
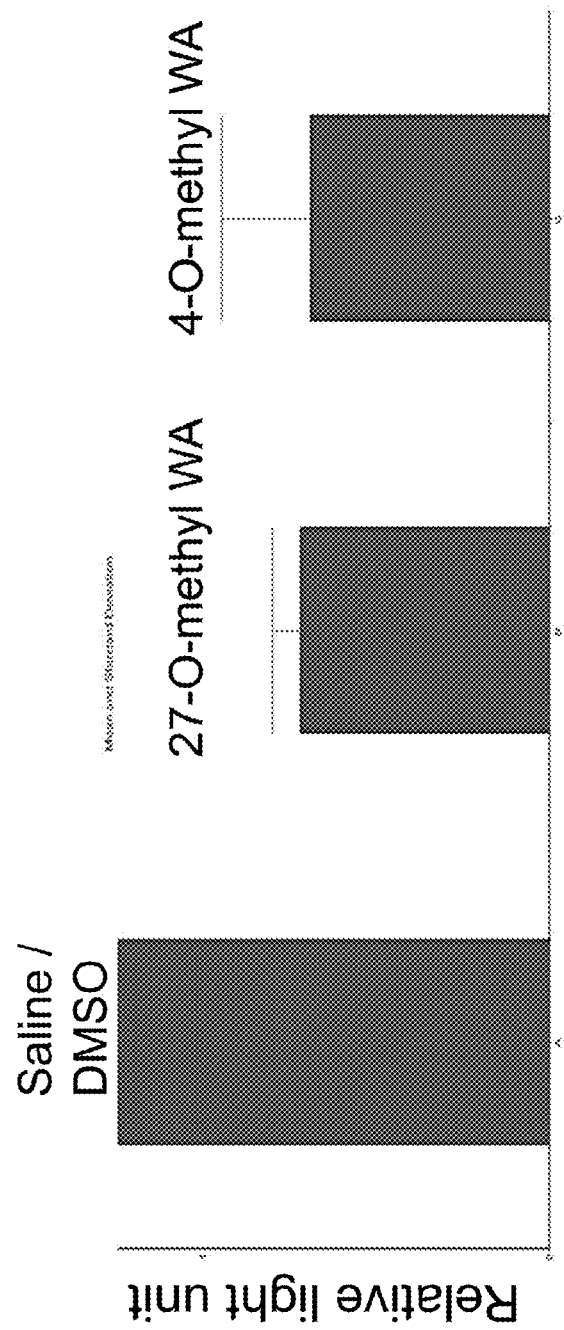
FIG. 1B is a bar graph showing the relative intensity of the bioluminescense of the brain images from FIG. 1A.

The results showed a significant decrease in the bioluminescent signal in mice treated with either 4-O-methyl WA or 27-O-methyl WA compared to mice treated with saline-DMSO alone (FIG. 1A). FIG. 1B shows a summary graph of the quantification of the luciferase activity expressed as counts of total photon emission in the brain of the GFAP-transgenic mice shown in FIG. 1A. This experiment demonstrated a significant reduction in astrogliosis in GFAP-transgenic mice treated with either 4-O-methyl WA or 27-O-methyl WA.

Example 3

Novel withanolides inhibit NF-κB reporter activity in BV2 microglial cells stimulated with LPS. The withanolides 4-O-methyl WA, 27-O-methyl WA and 4,27-O-dimethyl WA were tested for their ability to inhibit NF-κB activation. An NF-κB specific luciferase reporter system in BV-2 microglial cells was first established. This cell line was generated by stable transfection of BV-2 cells with stable insertion of a luciferase reporter 4 kBwt luciferase plasmid and subsequent selection with hygomycin. LPS was used to stimulate NF-κB activity in these cells. Twenty-five thousand hygromycin B-resistant BV-2 cells were seeded per well in 24-well dishes and allowed to adhere overnight. The next morning, the culture medium (DMEM+10% FBS) was removed and 1 ml of fresh medium (DMEM without FBS) added to each well. The stock solutions of withanolides (2 mg/ml in DMSO) were diluted in 1×PBS to various concentration (0.05 to 5 uM) and added to the wells. LPS was added one hour later at a final concentration of 100 ng/ml. Four hours later, the BV-2 cells were rinsed with 1×PBS prior to proceeding with the luciferase assay that was performed according to the manufacturer's instructions (Bright-Glo™ luciferase assay system, Promega, Wis.).

Figure 2:
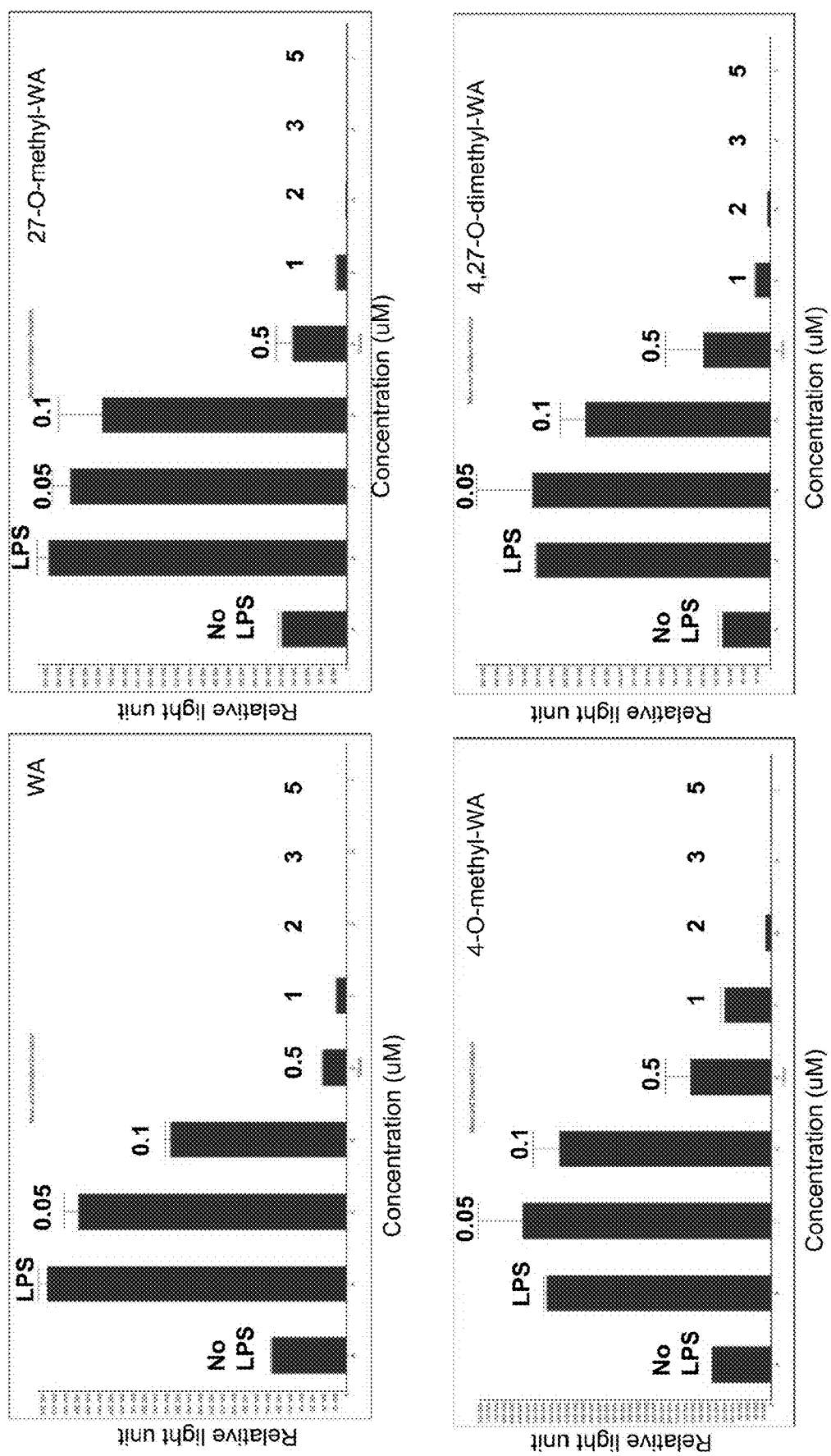
FIG. 2 includes bar graphs showing the effect of different concentration of withanolides 4-O-methyl WA, 27-O-methyl WA and 4, 27-O-dimethyl A on NF-κB reporter activity in BV2 microglial cells stimulated with LPS.

The results, provided in FIG. 2, showed that all of the withanolides tested had the ability to inhibit NF-κB expression. Table 2 below shows the IC50 of certain compounds of Formula (Ia).

TABLE 2

| Compounds | IC$_{50}$ (μM) |
|---|---|
| 4-O-methyl WA | 0.97 |
| 27-O-methyl WA | 0.71 |
| 4,27-O-dimethyl WA | 0.80 |
| WA | 0.50 |

Example 4

Novel Withanolides Inhibit Up-Regulation of TNF-α-Induced Signalling Activity in the HEK293-NF-κB-Luciferase Reporter Cell Line Ten thousand hygromycin B-resistant HEK-293 cells were seeded per well in a 96-well plate (Corning, New- York) and allowed to adhere overnight. The next morning, the culture medium (DMEM+10% FBS) was removed and 100 ml of fresh medium (DMEM without FBS) added to each well. The stock solutions of withanolides 4-O-methyl WA, 27-O-methyl WA and 4,27-O-dimethyl WA (2 mg/ml in DMSO) were diluted in 1×PBS to various concentration (0.05 to 5 uM) and added to the wells. Human recombinant TNF-alpha (R&D Systems, Minneapolis) was added one hour later at a final concentration of 40 ng/ml. Four hours later, the HEK-293 cells were rinsed with 1×PBS prior to the luciferase assay, which was performed according to the manufacturer's instructions (Bright-Glo™ luciferase assay system, Promega, Wis.).

Figure 3:
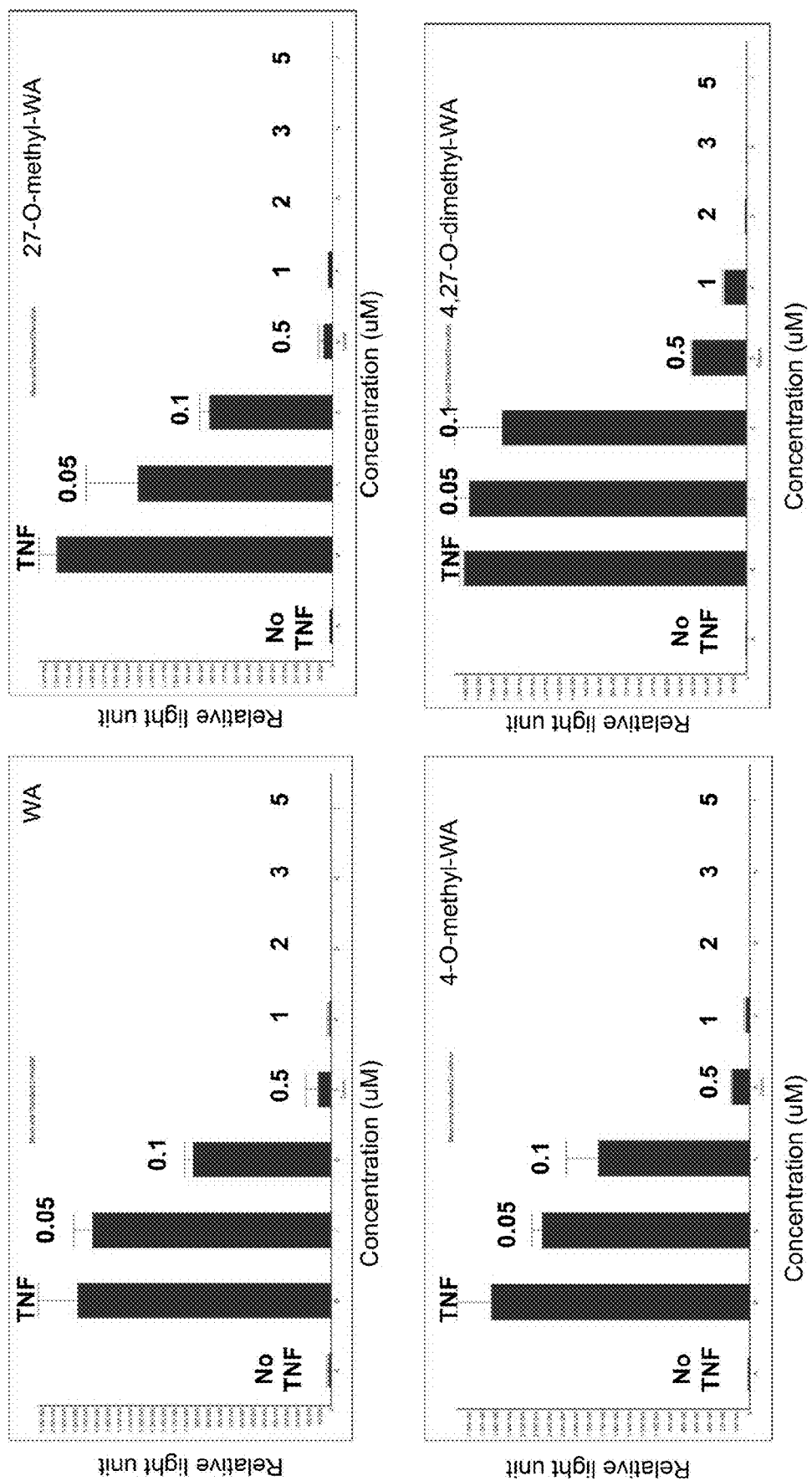
FIG. 3 includes bar graphs showing the effect of different concentrations of withanolides 4-O-methyl WA, 27-O-methyl WA and 4,27-O-dimethyl WA on the up-regulation of TNF-α-induced signalling activity in the HEK[293]-NF-κB-luciferase reporter cell line.

The results of the assay, shown in FIG. 3, confirmed that 4-O-methyl WA, 27-O-methyl WA and 4,27-O-dimethyl WA inhibited NF-κB expression. The $IC_{50}$s for 4-O-methyl WA, 27-O-methyl WA and 4,27-O-dimethyl WA are shown in Table 3.

TABLE 3

| Compounds | $IC_{50}$ (µM) |
| --- | --- |
| 4-O-methyl WA | 0.32 |
| 27-O-methyl WA | 0.26 |
| 4,27-O-dimethyl WA | 0.45 |
| WA | 0.34 |

Example 5

Safety Comparison of WA, 4-O-Methyl WA and 27-O-Methyl WA

An acute dose-escalation study was carried out to compare the tolerability in vivo of WA, 4-0 methyl WA and 27-0 methyl WA. Normal C57BL/6 female mice were injected intraperitoneally with WA, 4-O-methyl WA or 27-O-methyl WA at doses ranging from 20 to 65 mg/kg (20, 25, 30, 35, 45, 55 and 65 mg/kg). Animals were observed for signs of morbidity, mortality and clinical changes in behavior, breathing, heartbeat, hydration and other conditions (such as ascites, shock, severe diarrhea and hemorrhage) at 1 h, 6 h and 24 hours post-dosing. Body weight was measured pre-dosing and at 24 h.

The withanolides 4-O-methyl WA and 27-O-methyl WA both showed a much better safety profile than WA. The LD50 (lethal dose, 50%) was found to be 55 mg/Kg for WA. The same LD50 value (54 mg/kg) for WA was previously reported (Patwardhan et al., *Drug Discovery and Development*, (2006), edited by M. S. Chorghade, Wiley). In contrast, no mortality was observed when mice were administered 55 mg/kg of either 4-O-methyl WA or 27-O-methyl WA. At the highest dose tested in the study, 65 mg/kg, no mortality was observed for mice injected with either 4-O-methyl WA or 27-O-methyl WA. However, the animals in these groups did exhibit some weakness and a decrease in activity post-dosing.

Example 6

Withaferin a Analogs Inhibit Neurological Disease Development in a TDP-43 A315T Transgenic Mouse Model of ALS The impact of repeated dosing with 4-O-Methyl WA and 27-O-Methyl WA on the development of neurological disease in the TDP-43 A315T transgenic mouse model of ALS was evaluated. The TDP-43 A315T mouse model for ALS is fully described in Swamp, V et al., Brain 134: 2610-2626 2011. TDP-43 A315T mice begin to exhibit neurological deficits at about 9 months of age, as measured by their performance in a number of behavioral and motor function tests (Barnes maze test, accelerating rotarod test and passive avoidance test).

Male and female TDP-43 A315T mice of approximately 9 months and 25-55 gm were included in the study, and were randomly assigned to three groups, as follows:

Group 1 (n=6) received 4-O-Methyl WA at 5 mg/kg;
Group 2 (n=7) (the control group) received vehicle (2% polysorbate [Tween-80]/5% DMSO/93% saline); and
Group 3 (n=7) received 27-O-Methyl WA at 5 mg/kg.

All animals received i.p. injections of either vehicle or 5 mg/kg of the test WA analogs every 2 days for 15 weeks. The injection volume at 12.5 mL/kg was based on the body weight of each individual animal at the start of the study.

All animals were observed at least once daily throughout the study for clinical signs, and were individually weighed weekly before the rotarod test. There were no significant changes in body weight or clinical signs over the study period. After 15 weeks, the mice were sacrificed, and the expression of the mutant TPD-43A315T protein in the spinal cord of each mouse was confirmed by an antibody immunofluorescence or western blot test.

Accelerating rotarod (as described in Gros-Louis, F., et al. *Hum Mol Genet* 17, 2691-2702 (2008)) was performed prior to first dosing and at weekly interval during the study. Testing was performed at 4-rpm speed with 0.25 rpm/s acceleration. Each mouse was subjected to three trials per session. The number of seconds each mouse remained on the rotarod apparatus for each trial was recorded.

The results are shown in FIGS. 4A and 4B. FIG. 4A shows the best scores (of the three trials) for individual mice in each group. FIG. 4B shows a regression analysis of the data in FIG. 4A. The data show that the rotarod performance of the vehicle-treated group declined over the 15 week period. However, the performance of both the 4-O-Methyl WA- and 27-O-Methyl WA groups actually improved over that time period. The linear regression analysis showed statistical significance for both 4-O-Methyl WA (p value of 0.02) and 27-O-Methyl WA (p value of 0.02), but not for the vehicle (p value of 0.2).

The results also demonstrate that the mice were able to tolerate the administration of 5 mg/kg of the WA analogs every other day for 15 weeks, providing further evidence for the safety of the compounds.

Example 7

Larger-Scale Synthesis and Purification of 27-O-Methyl Withaferin A

27-O-methyl withaferin was prepared from withaferin A starting material and purified using the procedures outlined below.

1. Preparation of 4,27-bis-O-triethylsilylwithaferin A.

To a stirred solution of withaferin A (4.0 g) in N,N-dimethylformamide (40 mL) at 0° C. was added imidazole (2.31 g 4 eq.). Triethylchlorosilane (4.28 mL, 3 eq.) was added in small portions over approximately 5 minutes, and the resulting mixture was stirred under nitrogen at 0° C. for approximately 2 hrs. After the reaction was complete as determined by HPLC, methanol (2 mL) was added and the mixture was stirred for another 5-10 min. The reaction mixture was diluted with ethyl acetate (250 mL) and washed with brine (4×100 mL). The aqueous washings were combined and back extracted with ethyl acetate (2×100 mL). All ethyl acetate extracts were combined, washed again with brine (3×100 mL), dried with anhydrous sodium sulfate and concentrated to obtain 10 g of crude 4, 27-bis-O-triethylsilylwithaferin A as a pale oil.

2. Preparation of 4-O-Triethylsilylwithaferin A

Crude 4, 27-bis-O-triethylsilylwithaferin A (10 g) was dissolved in aqueous tetrahydrofuran (120 mL, THF/water, 9/1) at room temperature. Pyridinium p-toluenesulfonate (PPTS, 120 mg) was added. The mixture was stirred for approximately 13 hours, during which additional PPTS (approximately 145 mg) was added in 6-30 mg portions to the reaction in 1 hour intervals. The reaction progress was closely monitored by HPLC. After the reaction was complete, the mixture was diluted with ethyl acetate (300 mL) and washed with brine (5×100 mL). The aqueous washings were combined and back extracted with ethyl acetate (2×50 mL). All ethyl acetate extracts were combined, washed with brine (100 mL), dried with anhydrous sodium sulfate, and concentrated to yield a crude product (11.5 g) as a pale gum. The crude product was purified by silica gel column chromatography (dichloromethane/acetone 95-93/5-7) to afford 4.2 g of pure 4-O-triethylsilylwithaferin A.

3. Preparation of 27-O-Methyl-4-O-Triethylsilylwithaferin A

4-O-triethylsilylwithaferin A (1.0 g) was dissolved in a mixture of anhydrous THF (40 mL) and methyl iodide (8 mL) and cooled in an ice-water bath under nitrogen. Sodium hydride (60% in mineral oil, 108 mg, 1.58 eq.) was added and the mixture was stirred at room temperature for 4 minutes. The mixture was then stirred at room temperature for approximately 1 hour 40 minutes, during which the reaction was closely monitored by HPLC. After the product had reached 20-30%, the mixture was diluted with ethyl acetate (200 mL) and washed with brine (3×80 mL). All washings were combined and back extracted with ethyl acetate (2×50 mL). All ethyl acetate extracts were combined, washed with 10% aqueous sodium thiosulfate (50 mL), brine (2×80 mL), dried over anhydrous magnesium sulfate, and concentrated.

The crude product, pooled with another batch started with 0.5 g 4-O-triethylsilylwithaferin A, was purified by column (dichloromethane/acetone 95-93/5-7) to give 413 mg of 27-O-methyl-4-O-triethylsilylwithaferin A and 756 mg of recovered starting material. The average yield was about 27%.

4. Preparation of 27-O-Methylwithaferin A

27-O-methyl-4-O-triethylsilylwithaferin A (413 mg) was dissolved in a mixture of THF (9.5 mL) and pyridine (1.2 mL) and stirred in an ice-water bath. Pyridine hydrofluoride (0.85 mL) was added dropwise, and after 5 minutes at 0° C., the mixture was stirred at room temperature for 1.5 hr. The mixture was diluted with ethyl acetate (150 mL), washed with 0.1 N hydrochloric acid (50 mL) and brine (2×50 mL). The washings were combined and back extracted with ethyl acetate (2×50 mL). All ethyl acetate extracts were combined and washed with saturated sodium bicarbonate (50 mL), brine (2×50 mL), dried over sodium sulfate, and concentrated. The crude product was purified by silicagel column chromatography (hexane/acetone, 70-65/30-35) to yield 275 mg of 27-O-methylwithaferin A (>95% purity; 82% yield). The purified product was further recrystallized in acetone and hexane to increase the purity to approximately 99% as assessed by HPLC.

Example 8

Larger-Scale Synthesis and Purification of 4-O-Methylwithaferin A

4-O-methylwithaferin A was prepared from withaferin A starting material and purified using the following procedures.

1. Preparation of 27-O-(tert-butyldimethylsilyl)withaferin A

Withaferin A 5.6 g were dissolved in 60 mL of dichloromethane. Triethylamine (4.0 mL) was added to the mixing solution followed by the addition of 4.01 g of tert-butyldimethylchlorosilane. The solution was stirred at ambient temperature for approximately 80 hrs. The solution was washed with water and concentrated to give 6.95 g of crude 27-O-(tert-butyldimethylsilylwithaferin A. This was crystallized from methanol and dried to give 5.6 g of 27-O-(tert-butyl.dimethylsilywithaferin A with an HPLC purity of 99.5%. Shorter reaction times can be achieved by the addition of 0.5 g of dimethylaminopyridine leading to 95% completion in 12 hours.

2. Methylation of 27-O-(tert-butyldimethylsilyl)withaferin A 4.0 g of 27-O-(tert-butyldimethylsilyl)withaferin A was placed in a round bottom flask under nitrogen. 20 mL of anhydrous N,N-dimethylformamide were added to the flask. Dissolution of the solids was incomplete, but addition of 10 mL of methyl iodide yielded a clear solution. Sodium hydride (0.32 g, 60% in mineral oil) was added into the mixing solution over 10 minutes. HPLC showed approximately 80% completion. An additional 0.5 g of sodium hydride was added to achieve 99% completion. Acetic acid was used to quench remaining sodium hydride. The mixture was diluted with dichloromethane and washed with water. The organic layer was concentrated to 20 mL. HPLC showed 88% purity of 4-O-methyl-27-O-(tert-butyldimethylsilyl)withaferin A.

3. Preparation of 4-O-Methylwithaferin A

The solution of 4-O-methyl-27-O-(tert-butyldimethylsilyl)withaferin A obtained above was transferred to a PTFE flask rinsing forward with 30 mL of dichloromethane. Pyridine (3 mL) was added, followed by 1 mL of pyridine hydrofluoride. The reaction was monitored by HPLC. After 5.5 hours, an additional 0.5 mL of pyridine hydrofluoride was added. The reaction continued for another 3 hours to 92% completion. The reaction was worked up by washing the organic solution with water, then sodium bicarbonate solution, and finally sodium chloride solution. The dichloromethane layer was concentrated on a rotary evaporator to give a viscous liquid. This was diluted with 36.5 mL of dichloromethane and 36.5 mL methanol and washed with 73 mL water. The organic layer was concentrated under vacuum to give 3.9 g of crude 4-O-methylwithaferin A.

4. Purification of the 4-O-Methylwithaferin A

The crude 4-O-methylwithaferin A obtained above was dissolved in dichloromethane and loaded onto a 100 g silicagel column packed with dichloromethane. The column was eluted with 30% v/v acetone in dichloromethane. The fractions were analyzed by HPLC and those containing pure product were combined and evaporated to give 1.8 g of solids at 97% purity. The solids were crystallized from a mixture of 5 mL methanol and 10 mL methy-tert-butylether. The solids were dried in a vacuum oven to give 0.61 g of 4-O-methylwithaferin A at 98% HPLC purity.

The various embodiments described above can be combined to provide further embodiments. All of the U.S.

patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating amyotrophic lateral sclerosis in a patient comprising administering to the patient a therapeutically effective amount of a compound Formula (Ia):

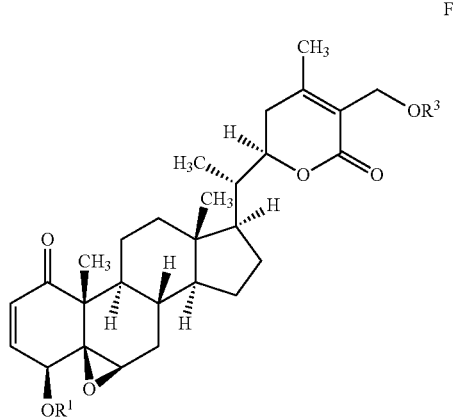

Formula (Ia)

wherein:
$R^1$ is hydrogen, or methyl; and
$R^3$ is hydrogen, or methyl,
wherein, $R^1$ and $R^3$ cannot both be hydrogen.

2. The method of claim 1, wherein $R^1$ is methyl and $R^3$ is hydrogen.

3. The method of claim 1, wherein $R^1$ is hydrogen and $R^3$ is methyl.

4. The method of claim 1, wherein $R^1$ is methyl and $R^3$ is methyl.

5. A method of administering a compound to a patient, comprising: administering to the patient a compound Formula (Ia):

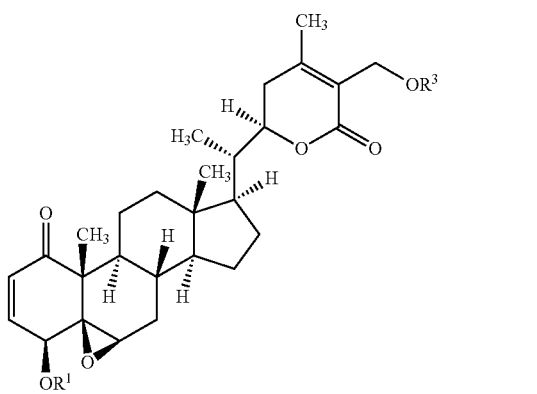

Formula (Ia)

wherein:
R1 is hydrogen, or methyl; and
R3 is hydrogen, or methyl,
wherein, R1 and R3 cannot both be hydrogen,
wherein the patient is identified as having a disease characterized by a TDP-43 proteinopathy selected from the group consisting of: amyotrophic lateral sclerosis, Alzheimer's disease, Parkinson's disease, and frontotemporal lobar degeneration.

6. The method of claim 5, wherein $R^1$ is methyl and $R^3$ is hydrogen.

7. The method of claim 5, wherein $R^1$ is hydrogen and $R^3$ is methyl.

8. The method of claim 5, wherein $R^1$ is methyl and $R^3$ is methyl.

9. The method of claim 5, wherein the patient is identified as having amyotrophic lateral sclerosis.

* * * * *